United States Patent [19]

Hoftman

[11] Patent Number: 5,787,893

[45] Date of Patent: Aug. 4, 1998

[54] SURGICAL SPLASH SHIELD PREVENTION DEVICES

[76] Inventor: Moshe Hoftman, 22205 Dardenne Ave., Calabasas, Calif. 91302

[21] Appl. No.: 811,195

[22] Filed: Mar. 5, 1997

Related U.S. Application Data

[60] Provisional application No. 60/012,843 Mar. 5, 1996.
[51] Int. Cl.$^6$ ............................................. A61F 5/37
[52] U.S. Cl. ............................................. 128/846
[58] Field of Search ..................... 128/845, 846, 128/849–856; 359/811, 812, 819

[56] References Cited

U.S. PATENT DOCUMENTS 1,717,755  6/1929  Brady ........................ 359/812
2,104,198  1/1938  Jones ........................ 359/811
2,208,642  7/1940  Neuwirth .................... 359/812
5,262,899  11/1993  Iizuka ....................... 359/811

Primary Examiner—Michael A. Brown

[57] ABSTRACT

This invention is a splash prevention device adapted to prevent splashing or contamination by blood or body fluids substantially closer to the point of use than prior art devices. It is a further improvement over the prior art to provide in this invention magnifying means integral with the point of use splash prevention device, wherein the magnification means comprise a relatively inexpensive, light and disposable adaptation of one of the splash prevention devices.

1 Claim, 3 Drawing Sheets

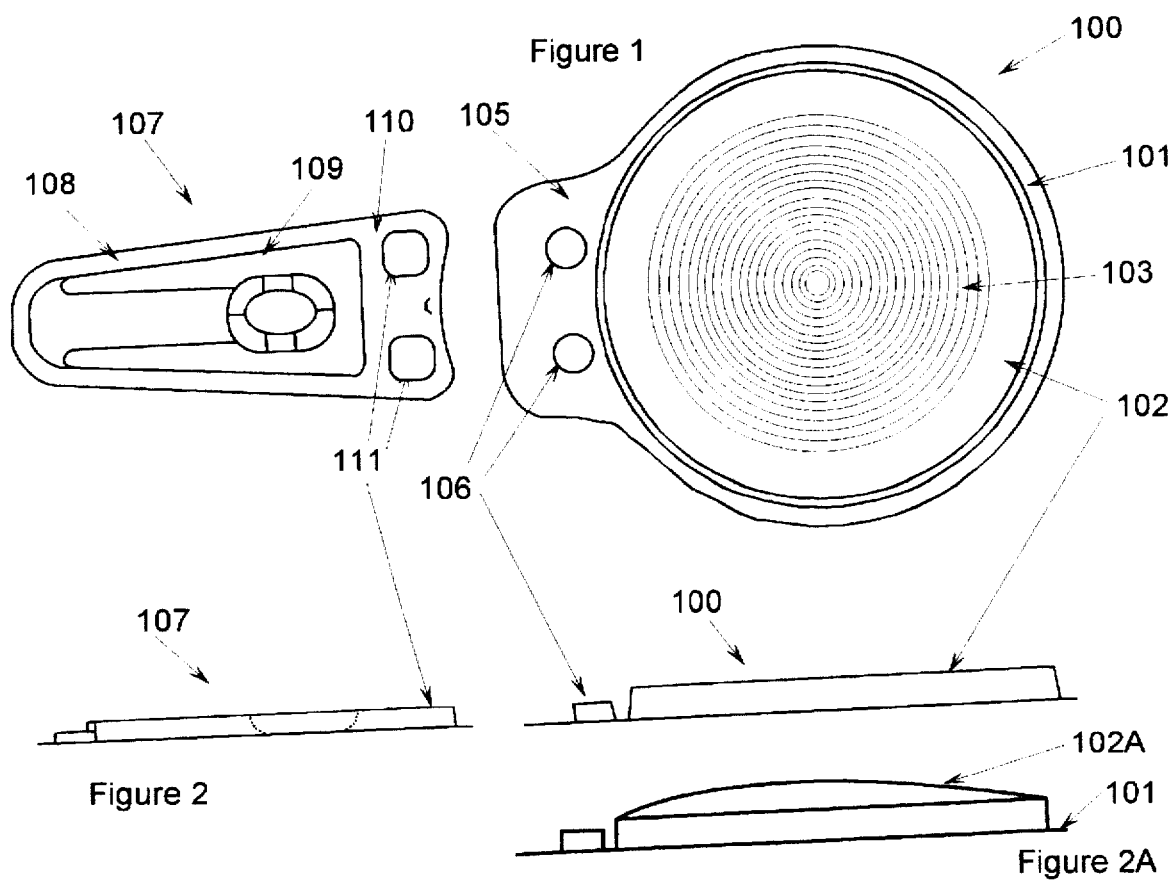
Figure 1
Figure 2
Figure 2A
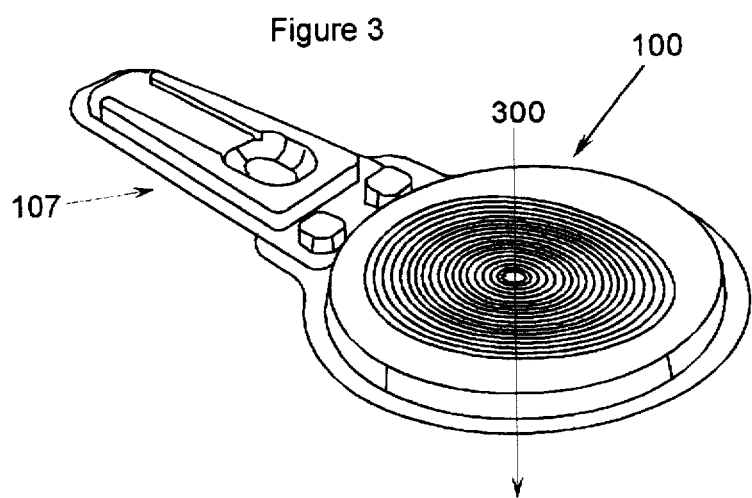
Figure 3

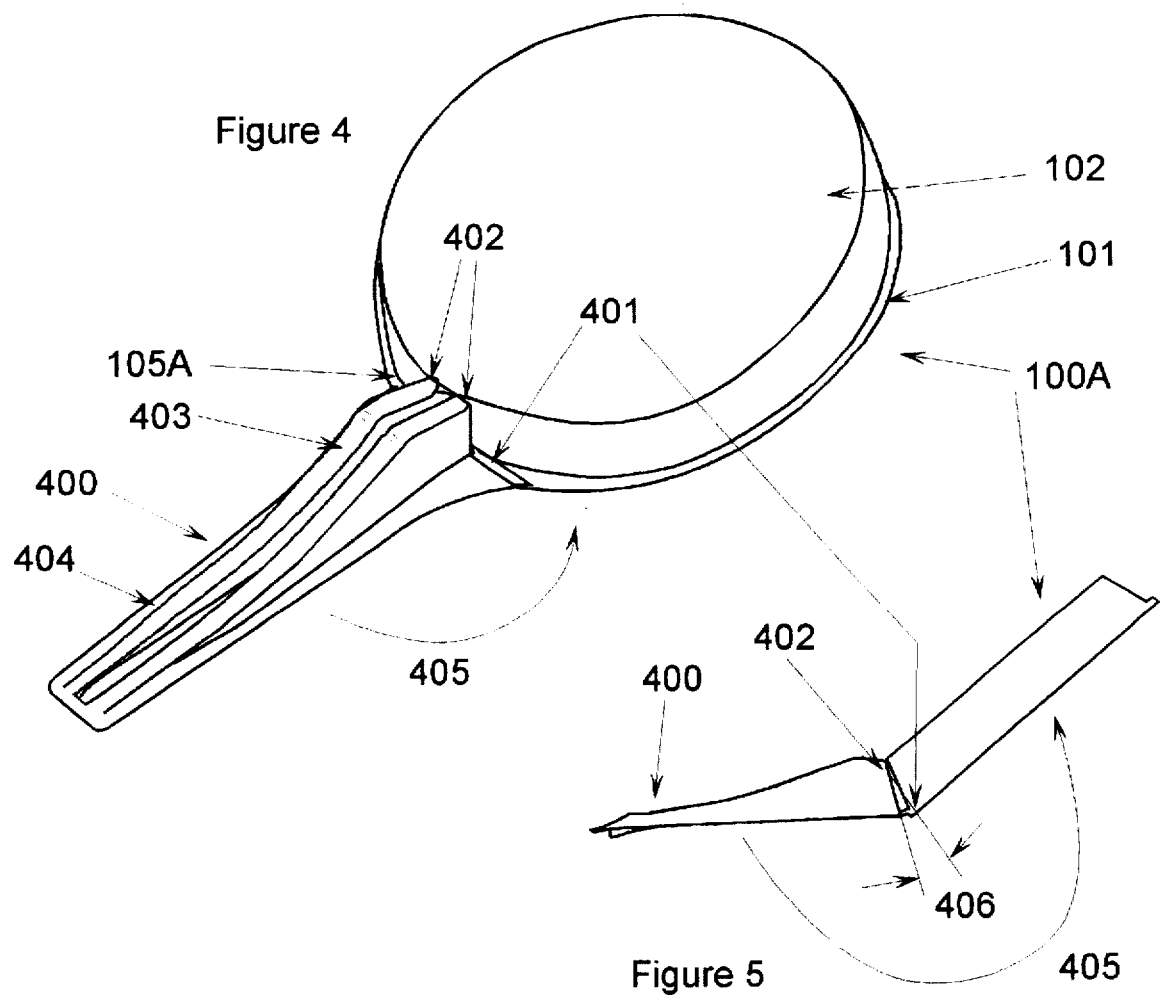
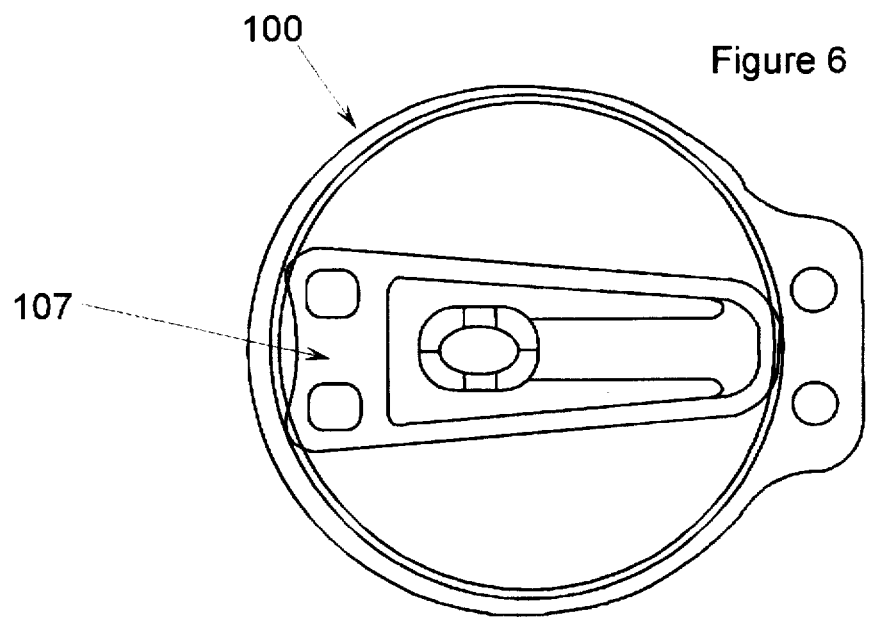

5,787,893

1

SURGICAL SPLASH SHIELD PREVENTION DEVICES

This application claims benefit of and incorporates herein the Provisional Patent Application No. 60/012,843 filed Mar. 5, 1996.

BACKGROUND OF THE INVENTION

The present invention relates to devices that protect against splashing of blood on the surgical staff during surgery.

In many surgical procedures, in particular, cardiovascular surgery, it is very common to get splashed with droplets or aerosolized blood while opening, manipulating or suturing pressurized blood vessels, such as in grafting or shunt replacement procedures. It is known in the prior art for the surgeon and nursing personnel to attempt to protect themselves from this potential source of blood borne pathogens with face shields attached to a face mask for eye protection.

SUMMARY OF THE INVENTION

This invention is a splash prevention device adapted to prevent splashing or contamination by blood or body fluids substantially closer to the point of use than prior art devices. It is a further improvement over the prior art to provide in this invention magnifying means integral with the point of use splash prevention device, wherein the magnification means comprise a relatively inexpensive, light and disposable adaptation of one of the splash prevention devices.

In one embodiment of the present invention, a round, extremely light guard portion of the splash prevention device incorporates magnification means. Magnification means preferably comprise a flat, thin Fresnel lens constituted by a series of spaced prismatic grooves each at a different angle and at a different depth formed in a clear plastic sheet of high clarity and integrally molded into or formed of the same plastic as that of the rest of the splash prevention device. This magnification is of tremendous benefit for the surgeon during the suturing of grafts onto veins and other procedures where magnification of about 1.5 to 6 times will substantially enhance the ease of the procedure. The present invention also comprises a method of sterile packaging of the splash prevention device into a compact design, wherein a detachable or hinged handle fits inside a raised annular rim on the round guard to save space and money. The user of the splash prevention device will, in operation of the device, attach the handle to or extends the handle by its hinge away from the round guard to support the main splash shield portion of the splash prevention device.

Different guard sizes will be provided for different surgical procedures, such as, orthopedic where bone sawing takes place and the guard will prevent bone dust and other particles from spreading across the surgical suite.

BRIEF DESCRIPTION OF THE DRAWINGS

FIG. 1 shows a top view of the circular guard and detached elongated handle of the splash prevention device of the present invention.

FIG. 2 shows side view of the circular guard and detached elongated handle of the splash prevention device of the present invention.

2

Figure 1A:
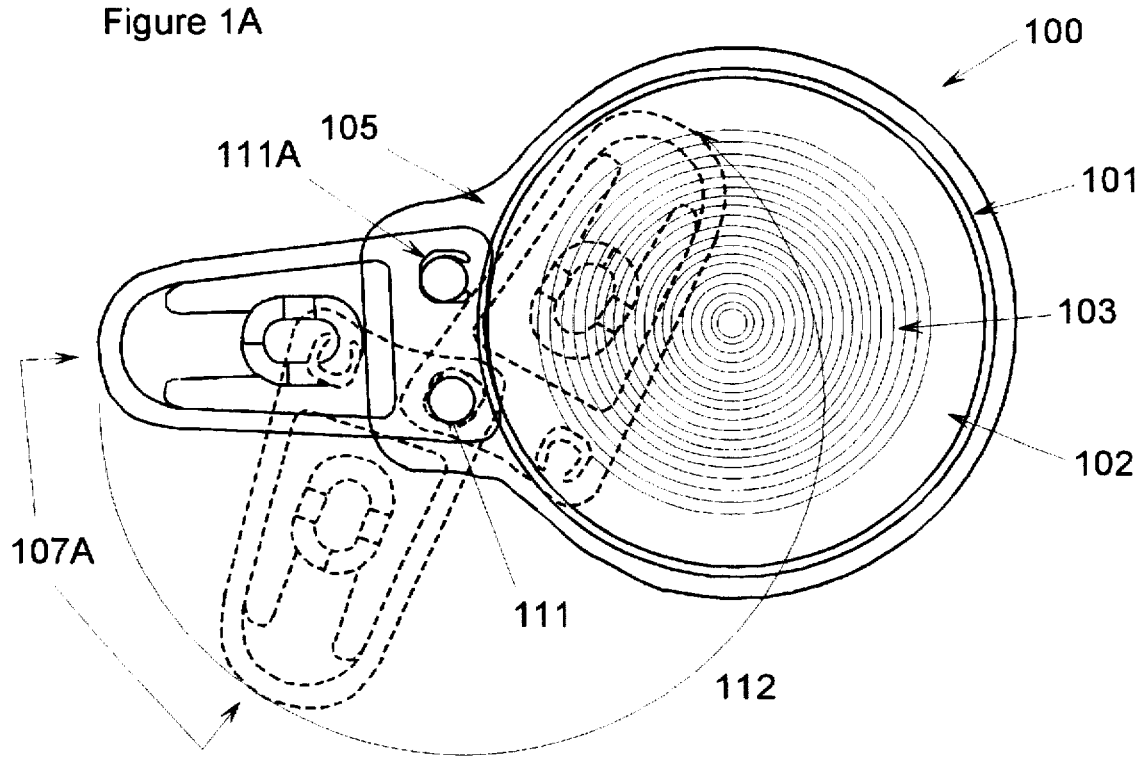
FIG. 1A shows a top view of the circular guard and an alternate embodiment of a detachable elongated handle of the splash prevention device of the present invention, wherein the swiveling path of the handle is shown from nesting position to operational position.

FIG. 2A is a side view of an alternate embodiment of the circular guard with a curved upper plane and sufficient thickness of the upper plane plastic to create magnification up to about 2X.

FIG. 3 shows an oblique angle perspective of the handle snapped onto the guard.

FIG. 4 shows an alternative embodiment of the splash prevention device of the present invention in which the handle is integrally part of the circular guard. The handle can be moved about a living hinge as shown to permit nested storage as shown for the detachable handle in FIG. 6.

FIG. 5 is a side view of the device of FIG. 4.

FIG. 6 shows the handle snapped inside the circular guard for placement in a pouch prior to sterilization for cost saving and convenient packaging.

DETAILED DESCRIPTION OF THE INVENTION

The splash shield prevention device of the present invention is now discussed with reference to the figures. Reducing size and cost while increasing utility of devices for surgical procedures is a goal achieved by the splash shield device of the present invention, which may weigh as little as 1-3 ounces with an overall length of about 9.5 inches. It is preferable to form the handle and guard of clear plastic sufficiently strong enough to support little more than its own weight, although the designs described herein will support much more than their own weight in the twisting or bending that might occur in surgical procedures.

In FIG. 1, it is seen that guard 100 is substantially round and preferably comprises a relatively thin plastic, such as polystyrene, polyethylene or polypropylene. It is an alternate embodiment that this guard is polygonal to accommodate specific procedures. A lower rim 101 supports the peripheral edge of guard 100. Upper plane 102 is supported above lower rim 101 and comprises the main body of the splash prevention surface. Fresnel lens 103 is preferably, although optionally provided, as integrally formed on the surface of upper plane 102. Lower rim extension 105 comprises an extension of lower rim 101 and further comprises hollow male lugs 106 extending in the direction of and are generally the same height as upper plane 102. Handle 107 is attachable to guard 100 by hollow female lugs 111 adapted to receive latchingly therein lugs 106. This latching connection adequately supports the guard 100 for positioning over a surgical site.

Handle 107 further comprises a lower rim 108 with extension 110 for support of lugs 111. Upper plane 109 is supported above lower rim 108 at slightly less than the height of upper plane 102 above lower rim 101, to permit storable and latchable nesting of handle 107 to the concave side of guard 100, as shown in FIG. 6. The differences in vertical height are seen in side views of handle 107 and guard 100 in FIG. 2.

It will be seen from FIG. 6 that handle 107 engages the concave, annular support of guard 100 between the upper plane 102 and lower rim 101. Thus, the pair may be carried or removed from a package without having the handle fall to the floor or become separated from the guard.

FIG. 3 shows an oblique angle view of guard 100 and handle 107 engaged by their respective lugs. It will be seen that the Fresnel lens integrated into the upper plane of guard 100 is adapted to magnify a surgical site when viewed in the direction of direction 300.

FIG. 4 generally comprises the guard 100 of FIG. 1, although shown as guard 100A. Lower rim extension 105A of FIG. 4 is much reduced over the lower rim extension 105 of FIG. 1 to accommodate the living hinge integrally connecting lower rim extension 105A to handle 400 at a portion of lower rim 404. Support section 403 comprises a hollow extension of lower rim 404 and is adapted to have a face which will contact a portion of the rising edge of lower rim 105A. The facial contact provides engageable support between the handle and the guard such that lugs similar to those shown in FIG. 1 may be used to secure the handle 400 in a desired angled relationship to guard 100A, as shown in FIG. 5. Angle 406 has been shown to be most effective for a broad range of surgical procedures at about 30°, although angling between 0°–40° can also be effective. It will be seen in FIGS. 4 and 5 that path 405 describes the hinged path of handle 400. Handle 400 is preferably adapted thereby to nest within a concave side of guard 101A similarly to the embodiment shown in FIG. 6, also providing therein on the concave side easily disengageable attaching means to secure in place the free end of handle 400.

Magnification means for the upper plane preferably accomplish only about 2X magnification of the surgical site for general surgical procedures. Higher magnification with hand held devices will be inherently less advantageous for longer procedures since slightly shaking or turning or the hand will cause the magnified view of the surgical site to shake or become skewed. It has been found that, as shown in FIG. 2A, making the upper plane 102A concave creates about 2X magnification of a surgical site in operation. It is preferred to thicken the upper plane 102A in an appropriate radial gradients from its center to enhance magnification.

In an alternate embodiment of the present invention as shown in FIG. 1A, a nesting of the handle is made in the guard portion where lug 106 is adapted to removably attach to lug 111 on handle 107A. In FIG. 1A, the guard portion is identical to that shown in FIG. 1, except that lugs 106 and lugs 111 and 111A are adapted to extend downward in relation to the top view as in FIG. 1A. Handle 107A is shown in solid lines in an operational position and in broken lines in a nesting position entirely beneath the guard 100 and in an intermediate position between nesting and operational positions. Path 112 describes the outer swiveling path of handle 107A as is swiveled about its lug 111 attachment to lug 106 on handle 100. Lug 111A is a horseshoe shaped lug which will engage the other lug 106 with moderate lateral pressure when handle 107A is moved into operational position. With this embodiment the handle need not be removed from the guard to bring the handle into operation position, an advantageous option reducing likelihood of dropping the handle or having problems engaging the lugs of the handle and the guard.

The above design options will sometimes present the designer with considerable and wide ranges from which to choose appropriate modifications for the above examples. However, the objects of the present invention will still be obtained by the skilled person applying such design options in an appropriate manner. For example, a substantial portion of the upper plane of the guard may be free of Fresnel lens magnification in a manner similar to a bifocal or a center portion of the circular lens may be eliminated leaving an annular magnification zone.

I claim:

1. A site proximal, hand held surgical splash guard comprising:
    (a) a guard comprising an upper plane and a peripheral lower rim, the upper plane comprising clear plastic and magnification means; and
    (b) a handle adapted to support the guard over a surgical site and nestable within a concave surface of the guard.

* * * * *